United States Patent
Anneren et al.

(10) Patent No.: US 9,845,455 B2
(45) Date of Patent: Dec. 19, 2017

(54) METHOD FOR CELL EXPANSION

(71) Applicant: GE HEALTHCARE BIO-SCIENCES AB, Uppsala (SE)

(72) Inventors: Cecilia Anneren, Uppsala (SE); Christian Kaisermayer, Uppsala (SE); Mats Lundgren, Uppsala (SE); Johanna Tschop, Uppsala (SE); Therese Lundstrom, Uppsala (SE); Ann-Christin Magnusson, Uppsala (SE); Gerald Blueml, Kapfenberg (AT)

(73) Assignee: GE Healthcare Bio-Sciences AB, Uppsala (SE)

(*) Notice: Subject to any disclaimer, the term of this patent is extended or adjusted under 35 U.S.C. 154(b) by 111 days.

(21) Appl. No.: 13/866,169

(22) Filed: Apr. 19, 2013

(65) Prior Publication Data
US 2013/0236970 A1  Sep. 12, 2013

Related U.S. Application Data

(63) Continuation-in-part of application No. 12/991,930, filed as application No. PCT/SE2009/050517 on May 11, 2009, now abandoned.

(30) Foreign Application Priority Data

May 15, 2008 (SE) ................................ 0801117

(51) Int. Cl.
| | |
|---|---|
| C12N 5/00 | (2006.01) |
| C12N 5/0775 | (2010.01) |
| C12M 1/00 | (2006.01) |
| C12M 1/12 | (2006.01) |

(52) U.S. Cl.
CPC .......... *C12N 5/0075* (2013.01); *C12M 23/14* (2013.01); *C12M 23/34* (2013.01); *C12M 25/16* (2013.01); *C12M 47/02* (2013.01); *C12N 5/0663* (2013.01); *C12N 5/0675* (2013.01)

(58) Field of Classification Search
None
See application file for complete search history.

(56) References Cited

U.S. PATENT DOCUMENTS

| | | |
|---|---|---|
| 3,282,411 A | 11/1966 | Jardine |
| 6,354,444 B1 | 3/2002 | Mahendran et al. |
| 7,490,451 B2 | 2/2009 | Matthews |
| 7,531,120 B2 | 5/2009 | Van Rijn et al. |
| 8,201,485 B2 | 6/2012 | Lee et al. |
| 2004/0058436 A1* | 3/2004 | Zhang .................. C12M 27/02 435/295.1 |
| 2006/0205071 A1* | 9/2006 | Hasson et al. ............... 435/366 |
| 2007/0264713 A1 | 11/2007 | Terstegge et al. |

FOREIGN PATENT DOCUMENTS

WO   WO 2010/036338   4/2010

OTHER PUBLICATIONS

Eibl et al. Cell and Tissue Reaction Engineering, Sep. 30, 2008, Chapters 3 and 4 p. 55-102.*
Justice et al. 3D Cell Culture Opens New Dimensions in Cell-Based Assays, Jan. 2009, Drug Discovery Today, vol. 14 No. 1/2, p. 102-107.*
GE Healthcare, Microcarrier Cell Culture: Principles and Methods, GE Healthcare, 2005 pp. 75-80; 114-115; 144 Full document is available online—scans of relevant pages are provided. http://www.gelifesciences.com/aptrix/upp00919.nsf/Content/180CFF1511F005C9C1257628001CBE22/$file/18114062AB.pdf.*
Frauenschuh et al., A Microcarrier-Based Cultivation System for Expansion of Primary Mesenchymal Stem Cells; Biotechnol. Prog. vol. 23, pp. 187-193, 2007.*
Blüml, Gerald. "Microcarrier cell culture technology." Animal Cell Biotechnology. Humana Press, 149-178, 2007.*

* cited by examiner

*Primary Examiner* — Addison D Ault
(74) *Attorney, Agent, or Firm* — Wood IP LLC (57) ABSTRACT

The present invention relates to a method for cell expansion. More closely, it relates to a method for expansion of cells, such as mesenchymal stem cells, on microcarriers in a plastic bag bioreactor. The invention enables expansion to therapeutic amounts of stem cells. The method comprises the following steps: a) addition of cells in cell culture medium and microcarriers to a plastic bag container; b) allowing the cells to adhere to the microcarriers while the container is kept substantially still; c) addition of further cell culture medium once the cells have adhered; d) culturing the cells under gentle and constant agitation; e) increase the surface area for continued culturing; and f) final harvesting of cells by an active detachment and separation step.

16 Claims, 8 Drawing Sheets

METHOD FOR CELL EXPANSION

CROSS-REFERENCE TO RELATED APPLICATIONS

This application is a continuation-in-part of U.S. patent application Ser. No. 12/991,930 filed Nov. 10, 2010, which is a filing under 35 U.S.C. 371 of international application number PCT/SE2009/050517, filed May 11, 2009, published on Nov. 19, 2009 as WO 2009/139703, which claims priority to Swedish patent application number 0801117-3 filed May 15, 2008; the disclosures of which are incorporated herein by reference in their entireties.

FIELD OF THE INVENTION

The present invention relates to a method for cell expansion. More closely, it relates to a method for cell expansion of adherent mammalian cells, such as primary cells, cell lines or stem cells, e.g. mesenchymal stem cells, on microcarriers in a plastic bag bioreactor.

BACKGROUND OF THE INVENTION

Cell culture and expansion is a very important step in cell therapy and mesenchymal stem cells (MSCs) represent the second most selected stem cell group (after haematopoietic stem cells) in the adult stem cell market today.

A recent upsurge in the use of primary and stem cells (e.g. MSCs) for cell based therapy has created a growing need for cell culture systems that can be used to expand these cell types. Typically, MSCs are grown in monolayer T-flask cultures, which is labor intensive and space requiring if large amount of cells are to be produced. There is one article describing successful culture of porcine bone-marrow derived MSCs on microcarriers in spinner flasks (Frauenschuh, S., E. Reichmann, et al. (2007). "A Microcarrier-Based Cultivation System for Expansion of Primary Mesenchymal Stem Cells." *Biotechnol Prog* 23(1): 187-193.) However, this is not a disposable system and the shear forces from the mechanical mixing may damage the cells.

Previous published results have shown that it is possible to expand various types of cells (e.g. Vero cells and MDCK cells) on microcarriers in the Wave Bioreactor (Genzel, Y., R. M. Olmer, et al. (2006). "Wave microcarrier cultivation of MDCK cells for influenza virus production in serum containing and serum-free media." *Vaccine* 24(35-36): 6074-87.). The applications for these cultures lie in the vaccine production area, where there still is a need for improved productivity for cultivation methods with better scalability. The vaccine protocols cannot be fully applied to primary cell cultivation since they differ from cancer cell lines in several ways. For instance, MSCs and other stem cells are more sensitive and proliferative properties are limited as they lose their multilineage capacity after certain number of passages.

US 2007-0264713 relates to a method for proliferating stem cells on microcarriers. The stem cells, the microcarriers as well as culture medium are introduced into a container which could be a spinner flask or a bioreactor. An intermittent agitation technique is used in the method, wherein the medium is moved between 10 and 100 minutes and not moved between 10 and 60 minutes. The method is said to provide large yields of stem cells.

However, there is still a need of a new method suitable for expanding adherent cells, such as primary cells and stem cells, in bioreactors, for clinical scale production.

SUMMARY OF THE INVENTION

The present invention relates to cell expansion by a method capable of starting from a small volume with a low number of cells and ending with high numbers of cells suitable for, for example, cell therapy or vaccine antigen production.

The invention relates to a method for cell expansion, comprising the following steps: a) addition of cells in cell culture medium and microcarriers to a plastic bag container; b) allowing the cells to adhere to the microcarriers while the plastic bag container is kept substantially still; c) addition of further cell culture medium once the cells have adhered; d) culturing the cells under gentle and constant agitation, preferably to 70-80% confluency; e) increase the surface area for continued culturing through either an active detachment step of cells from the microcarriers followed by addition of new carriers, or by adding new carriers and allowing spontaneous migration of cells to these and f) final harvesting of cells by an active detachment and separation step.

The active detachment step in e) may, for example, be by allowing the cells to detach by using enzymes, thermo responsive agents, pH responsive agents, chelating agents or osmolality-changing agents. Enzymatic detachment may be provided e.g. by addition of trypsin or other suitable proteases. Alternatively, the cells are expanded by allowing passive migration from confluent beads to newly added beads.

Step b) may optionally be performed with intermittent or occasional rocking under very low speed, more gentle than in step c). It may alternatively be carried out under a constant rocking rate.

When step e) includes an active detachment step, the microcarriers may be conveyed to an external separation device for separation of the microcarriers from the detached cells. The external separation device can also be used for detachment, e.g. by addition of enzymes to the device. It is also possible to use the external separation device in the final cell harvesting step f).

Preferably, the step e) is repeated at least once.

In one embodiment, the core of microcarriers are provided with magnetic particles to facilitate sedimentation and/or decantation of culture media etc.

It is critical that the volume in step a) is low to increase cell-to-microcarrier contact and preferably, the volume of the added cells and microcarriers in step a) is between 150-300 ml. Seeding density is 1-10 cells per microcarrier and the start amount of microcarrier should be at least 0.2 g (dry weight) per liter.

The cells are adherent cells, such as primary cells, cell lines or stem cells. The stem cells may be adult or embryonic or induced pluripotent stem cells, iPS. The cells may be e.g. nucleated cells from adipose tissue, bone marrow or cord blood.

In one embodiment, the cells are pre-cultivated before step a). This is preferably done in a separate container, such as a culture flask.

In a preferred embodiment, the cells are adult mesenchymal stem cells. In a preferred embodiment, a final 3-5 g (dry weight) microcarriers per liter are present, which leads to a final cell number of 300-500×$10^6$ MSCs in a 1 liter bioreactor.

Preferably steps e) and f) are repeated until 3-8 g microcarriers per liter medium is reached. Up to 5 g without perfusion and up to 8 g with perfusion of the bioreactor bag with fresh medium etc.

In another embodiment, the MSCs may be obtained from a purified blood (mononuclear cell fraction) or tissue sample, without any pre-cultivation. Thus, these cells may be provided directly into the above workflow.

In yet another embodiment the cells are mammalian cells, e.g. Vero or MDCK cells, which are infected with a virus. They can then be used for production of virus antigens to be used in a vaccine or for production of gene therapy virus vectors.

Preferably, the container is an inflated bioreactor bag. The cultivation may be performed under hypoxic conditions.

The cells may be detached in step e) inside the container or outside the container. In the latter case the cells and microcarriers are re-introduced into the container.

The final harvest of the expanded cells is preferably performed by the same principle as detachment outside the bag which is described more closely in the detailed section below.

BRIEF DESCRIPTION OF THE DRAWINGS

FIG. 4 shows the migration of adipose-derived human MSCs on CYTODEX™ 3 microcarriers in a WAVE™ plastic bag bioreactor after 4-18 days. On day 0, 50% of the carriers were seeded with wildtype-hMSCs and 50% with GFP-expressing hMSCs. On day 1 all the carriers were pooled and the % of carriers with only wt-hMSCs and the % with only hMSCs-GFP or with additional wt-hMSCs were measured. Cells migrate to empty carriers and between carriers. Fresh empty carriers were added at 11 days and at 13 days. a) Carriers with only hMSCs-GFP or with additional wt-hMSCs, b) Carriers with only wt-hMSCs, c) Empty carriers

DETAILED DESCRIPTION OF THE INVENTION

The invention will now be described more fully in association with the accompanying drawings. However, it is to be understood that the examples only are intended for illustrative purposes without limiting the scope of the invention.

In the experiments a bioreactor has been used which provides a closed disposable system. Cells are grown on microcarriers which are agitated by a gentle wave-like motion and the surface area is increased by adding new carriers to the cultures as the cells expand. The surface area per gram of the preferred microcarriers CYTODEX™ 1 and CYTODEX™ 3 is 4400 $cm^2$ for CYTODEX™ 1 and 2700 $cm^2$ for CYTODEX™ 3. CYTODEX™ microcarriers are examples of crosslinked polysaccharide microcarriers in that they comprise spherical crosslinked dextran particles derivatized with either diethylaminoethyl groups (CYTODEX™ 1) or collagen (CYTODEX™ 3).

One therapeutic cell dose of MSCs can be produced using one single 2 L bag. The method according to the invention is suitable for the production of therapeutic stem cells and for the production of viruses in bags up to 200-2000 L size.

Figure 5:
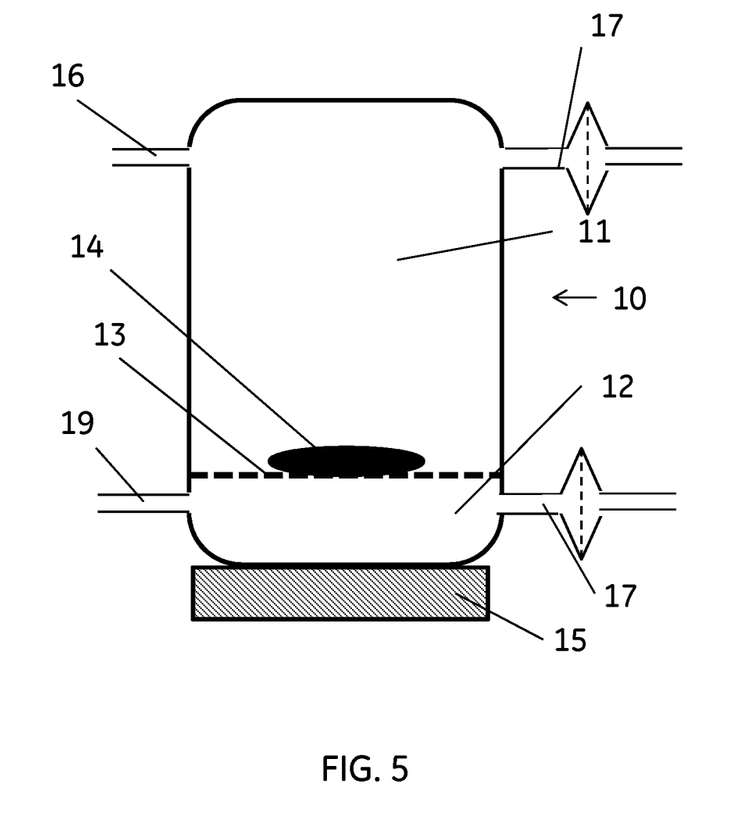
FIG. 5 shows one embodiment of an external separation device.
Figure 6:
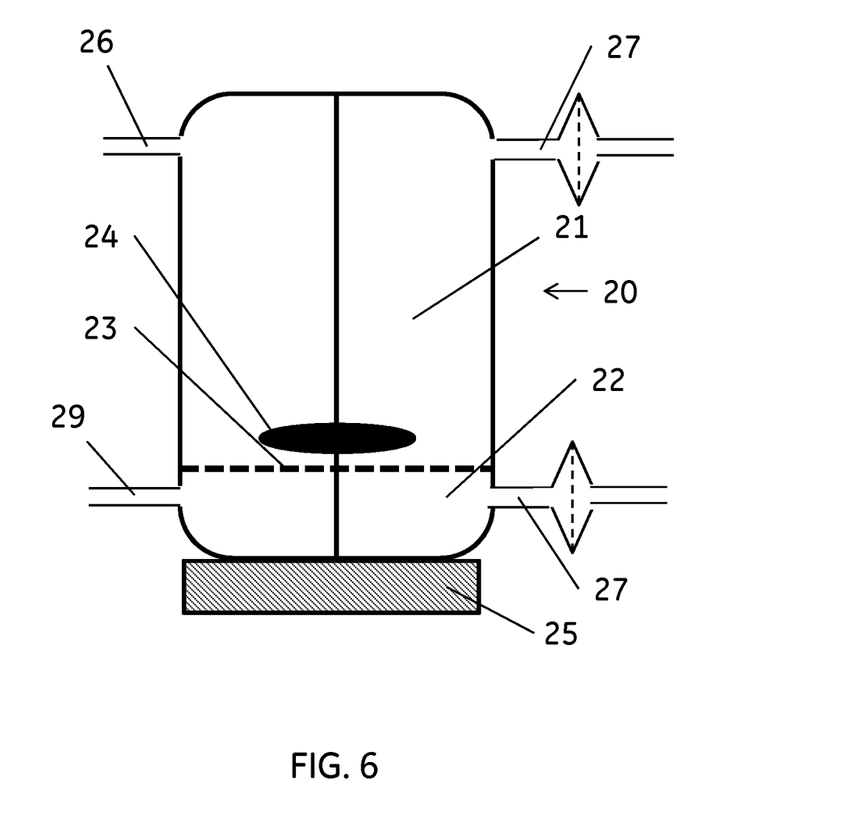
FIG. 6 shows an alternative embodiment of an external separation device.

The external separation device can be a stirred cell type device 10;20 as illustrated by FIG. 5 and FIG. 6. A vessel is divided into a retentate compartment 11;21 and a permeate compartment 12;22 by a screen (which can also be called a strainer or sieve) 13;23. Agitation can e.g. be provided by a rotating magnet 14;24, driven by a magnetic stirrer plate 15;25. In alternative embodiments, agitation may be provided by external motion, e.g. shaking or rocking, in which case no magnet is needed. When the microcarrier/cell suspension is fed into the vessel via the inlet 16;26, the detached cells pass through the screen 13;23 and are recovered via outlet 19;29, while the microcarriers are retained by the screen and stay in the retentate compartment 11;21. If a crossflow type separation is desired, the retentate compartment may further be fitted with an outlet (not shown) to allow for circulation of the suspension through the compartment The magnet can be located on the vessel bottom as in FIG. 5, but it can also be suspended on an axis as in FIG. 6, to diminish any tendency towards grinding of the cells. Both compartments may also be fitted with vent tubes 17;27 to facilitate filling of the device. The vent tubes are suitably equipped with hydrophobic vent filters. The screen is selected with pores of such a size and structure that detached cells pass though the pores, but the microcarriers do not.

As the diameters of mammalian cells typically are in the 5-15 µm range and microcarriers normally have diameters well above 100 µm, the pore size (average circle-equivalent pore diameter) of the screen can advantageously be in the 50-100 µm range. Suitable screens with pores in this size range can e.g. be woven or braided textile screens. To minimize retention of detached cells by the screen, it is advantageous if the pores are not tortuous (e.g. having an average tortuosity, defined as the average pore length divided by the average pore end-to-end distance, less than 1.5, such as less than 1.2) and a high open area, e.g. at least 10% or at least 25% open area. This can be achieved, e.g. by using single-layer woven screens with a square mesh weave pattern and distances between the threads approximatively equal to or exceeding the thread diameters. Alternatively it is also possible to use other types of parallel pore perforated microsieves as screens. This could e.g. be microsieves prepared by photolithography or polymer micromoulding as described in U.S. Pat. No. 7,531,120.

The external separation device can suitably be disposable, in which case it may be constructed mainly from plastics, such as e.g. thin flexible plastics or low-cost rigid plastics such as polystyrene. The vessel can be a flexible plastic bag and the screen may be a woven thermoplastic screen welded to the vessel walls. Inlets, outlets and vent tubes may be attached as ports welded to the relevant parts of the bag. The bag can be inflatable and/or it can be arranged to be self-supporting in a non-inflated state, e.g. by incorporating a foldable bottom sheet or by using a block-bottom pillow-top bag, according to methods known in the art of bags for packaging (see e.g. U.S. Pat. No. 3,282,411, U.S. Pat. No. 7,490,451 and U.S. Pat. No. 5,733,621).

The separation device 10;20 can be used in the orientation shown by FIG. 5 and FIG. 6, i.e. with the retentate compartment above the permeate compartment. It can however also be used in an inverted orientation, i.e. with the permeate compartment above the retentate compartment. In this orientation, gravity may assist the separation in that the larger and heavier microcarrier particles to some extent sediment towards the bottom of the retentate compartment, while the released cells follow the flow up to and through the screen into the permeate compartment. This will reduce any clogging of the screen by microcarrier particles. This effect can also be achieved in a fluidized bed operation mode. A skilled person will understand that some optimization of flow rates and agitation may be needed to achieve the best separation performance.

A further possibility is to operate the separation in one orientation during detachment of the cells and then shift the orientation for separation of detached cells and microcarrier particles.

Figure 7A:
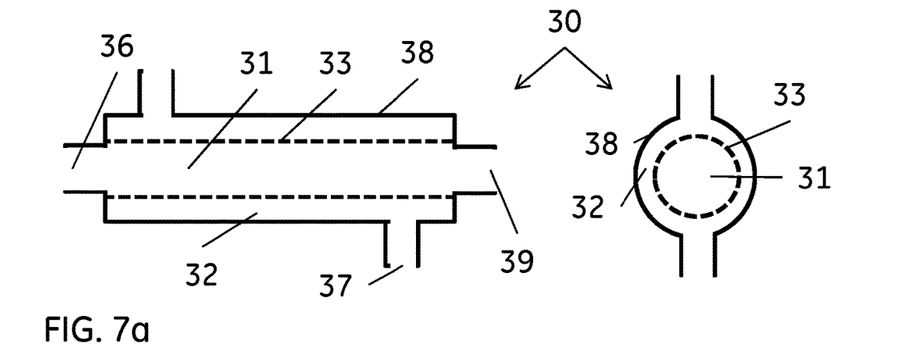
FIG. 7a and FIG. 7b show two further embodiments of external separation devices
Figure 7B:
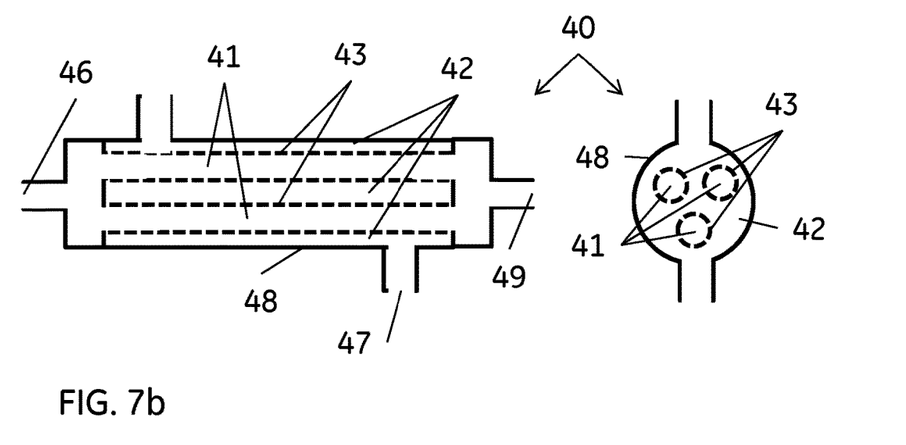

In alternative embodiments, the external separation device can be a tubular device 30;40 as illustrated by FIG. 7a and FIG. 7b. Such a device may comprise a single tubular screen 33 as in FIG. 7a or a plurality of tubular screens 43 as illustrated by FIG. 7b. In these devices the retentate compartment 31;41 may be the lumen(s) of the tubular screens and the permeate compartment 32;42 may be the volume between the tubular screen(s) and a wall 38;48 of the device. Alternatively, the permeate compartment may be the lumen(s) and the retentate compartment may be the volume between the tubular screen(s) and a wall of the device. The microcarrier/cell suspension can be fed into the device via an inlet 36;46 and if a crossflow type separation is desired it can exit the device via an outlet 39;49. The microcarriers are retained by the screen, while the detached cells can pass through the screen and be recovered via an outlet 39;49. In an alternative configuration, the microcarrier/cell suspension is fed via outlet 37;47 and the cells recovered via outlet 39;49 or inlet 36;46. In specific embodiments the devices may be designed as conventional tubular or hollow fiber membrane filtration modules, with the exception that one or more tubular screens are used instead of the membranes. In one embodiment, a device with a single tubular screen is integrated with a reciprocating pump to provide an alternating crossflow along the tubular screen. Such a device is described in WO 2010/036338 and is commercially available from Refine Technology (NJ) with a 70 μm tubular screen.

In the tubular devices 30;40, the demands on the screen(s) 33;43 are essentially the same as in the stirred cell devices 10;20 with respect to pore sizes and pore structures. Tubular screens may e.g. be manufactured by welding of flat screens to a tubular shape, in particular for tubular screens with a diameter above about 5 mm. It is however also possible to manufacture screens directly into a tubular shape e.g. by braiding or knitting of fibers. One example of such a tubular screen is the tubular braids suggested in U.S. Pat. Nos. 6,354,444 and 8,201,485 for use as support materials in hollow fiber manufacture. With an appropriate selection of fiber diameters and braiding technique, hollow fiber-like screens suitable for use in the current separation devices can be manufactured.

In the operation of the method, the following steps can be involved:
i) Initial cultivation, where
a) cells in cell culture medium and microcarriers are added to a plastic bag container;
b) the cells are allowed to adhere to the microcarriers; (for sensitive cells such as stem cells, this is suitably done while the plastic bag container is kept substantially still, while more robust cells such as Vero, MDCK or HEK cells will adhere also during agitation);
c) further cell culture medium is added once the cells have adhered;
d) culturing the cells are cultured under gentle and constant agitation, such as with up to 10 or up to 10 rpm rocking rate if a rocking bag-type bioreactor is used.
ii) Increasing the surface area for continued culturing through active detachment of cells from the microcarriers and addition of new carriers, where
a') microcarriers with cells are transferred from the bioreactor to the external separation device;
b') a buffer (e.g. PBS) or cultivation medium is flowed through the device to wash the cell-laden microcarriers. The cells and microcarriers are retained by the screen in the retentate compartment.
c') trypsin (or another protease) is added and the device is incubated at 37° for about 5-20 min under agitation.
d') buffer (e.g. PBS) is flowed through the device under agitation, so that the released cells pass through the screen into the permeate compartment while the cell-free carriers are retained.
e') fresh microcarriers are added and the cells are returned to the plastic bag container for further culture.

The operation can also include a final cell harvest step, which may also be carried out in the external separation device.

The transfer of microcarriers and cells to the separation device can suitably be performed through gravity flow or through an overpressure applied to the plastic bag container. This minimizes the risk of damage to the microcarriers by pumping.

EXPERIMENTAL PART

Example 1

A purified patient tissue sample of cells (approximately $1 \times 10^6$ MSCs) is pre-cultured in a T-flask to achieve an amount of $5\text{-}10 \times 10^6$ MSCs. The MSCs and 0.2-1 g dry weight (1-10 cells/bead) pre-swollen, sterilized CYTODEX™ (GE Healthcare Bio-Sciences AB), equilibrated in a commercially available MSC media, is added to an inflated 2 L WAVE™ bag (GE Healthcare Bio-Sciences).

The cells are allowed to adhere to the microcarriers either in the incubator during static conditions. Initially, media volume is kept low in the bag (150-300 ml) to increase cell-to-bead contact. Once the cells have attached, more media is added to achieve desired volume. During the culturing, a constant low rocking speed (<7 rpm) and rocking angle) ($\leq 5°$) is used. It is also possible to use rocking speeds up to about 10 rpm.

Figure 2:
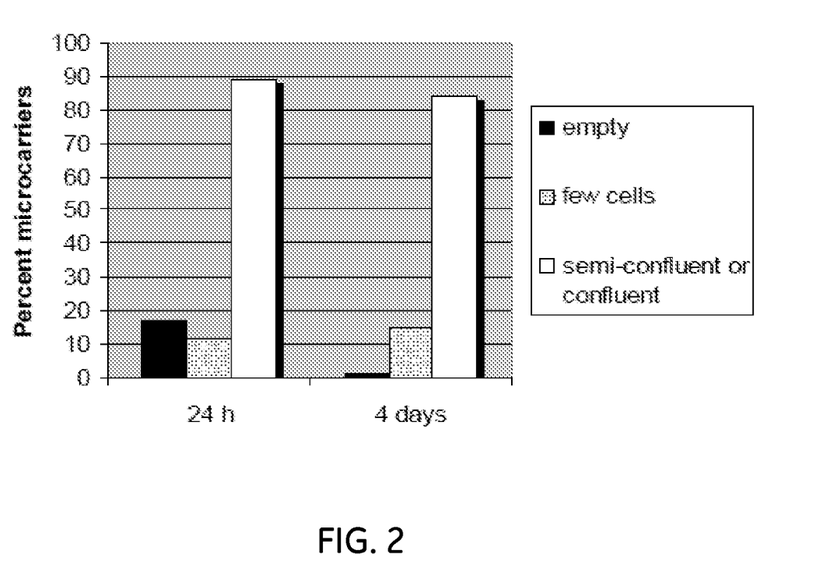
FIG. 2 shows the growth of bone marrow-derived MSCs on microcarriers in a plastic bag bioreactor after 1 day (A) and after 6 days (B), respectively. Cells migrate to empty carriers. Fresh empty carriers were added to an almost confluent MSC culture increasing the amount of carriers with 50% (e.g. 25% of all carriers were empty at time 0). After 24 hours 16% of the carriers were empty (black bars) and at 4 days only 1% empty carriers were found in the culture.
Figure 4:
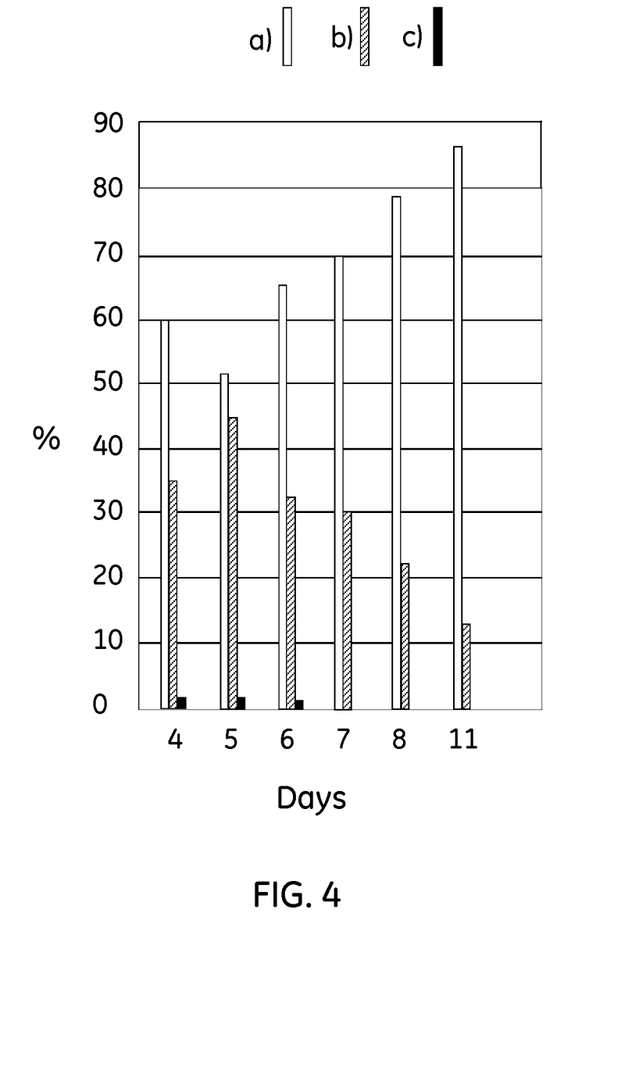

When the cells have reached 70-80% confluency (approximately one week culture period, see FIG. 2B), they are detached by e. g. a trypsin-based method. The trypsination can either be performed in the bag or the microcarriers can be transferred to an external bottle/smaller bag for trypsination. The trypsination can also be carried out in the external separation devices 10;20 as illustrated in FIGS. 4 and 5.

Figure 1:
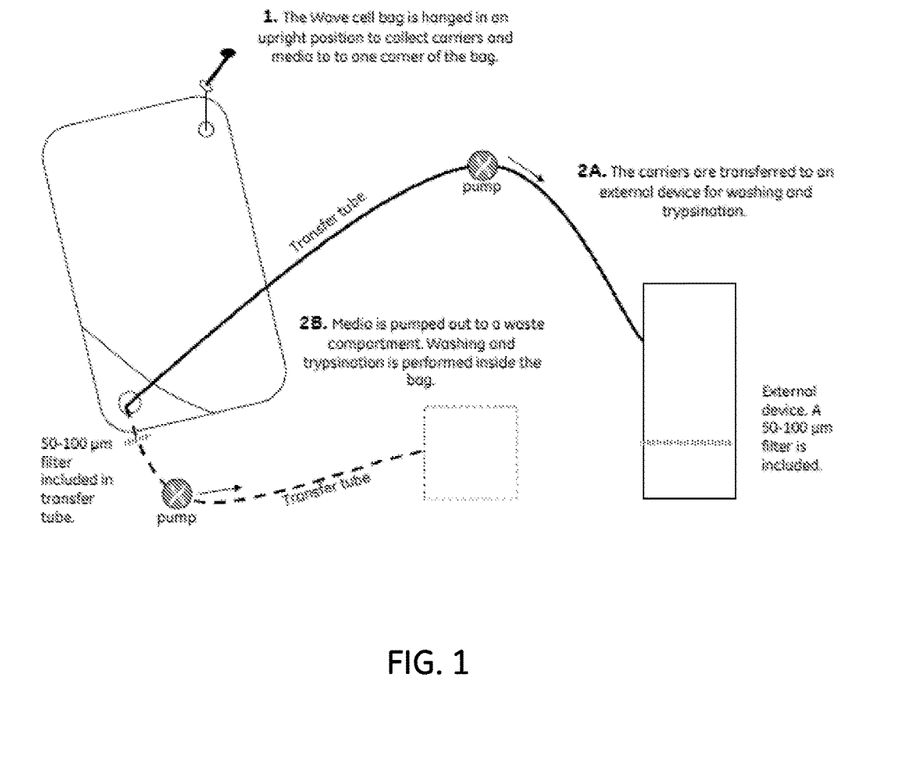
FIG. 1 shows the schematic view of a cell expansion bag put in an upright position, allowing the microcarriers to sediment down to one corner of the bag. The carriers are transferred to an external device for washing and trypsination (2A). Alternatively, media is pumped out from the bag while carriers remain in the bag by including a filter in the transfer tube (2B). Washing and trypsination are then performed inside the bag.

Outside the Bag:

The WAVE™ bag is put in an upright position, allowing the microcarriers to sediment down to one corner of the bag (FIG. 1 and FIG. 2). The carriers are transferred by gravity flow or pump to an external device, which includes a 50-100 µm filter for washing and trypsination steps. Advantage: easier to wash the carriers in an external device.

Inside the Bag:

The WAVE™ bag is put in an upright position and carriers are allowed to sediment down to one corner of the bag (FIG. 1 and FIG. 2). Media is removed and the washing and trypsination is performed inside the bag. Advantage: No removal of carriers and cells from the WAVE™ bag, thus, using one single compartment during the entire culture. To avoid complicated and time-consuming washing and to prevent loss of microcarriers, a 50-100 µm filter is inserted between the transfer tube of the bag and the waste outlet for media removal.

In both the above situations (outside and inside the bag, respectively) and in other cell cultivation situations where sedimentation is desired, the sedimentation of the microcarriers may be enhanced by adding magnetic particles, such as $Fe_2O_3$, to make the microcarriers more heavy, which also facilitates decanting of cell culture media etc. from the plastic bag. Even more efficient sedimentation and/or decanting is achieved if an external magnet is used to immobilize the microcarriers during the decanting procedure.

When trypsination is completed, new carriers are added to increase surface area and cells are allowed to attach once again for further proliferation. The detachment and subsequently the adding of new carriers and media is repeated until 3 gram CYTODEX™ carriers in one liter media is reached with a split ratio of approximately 1:3. The final harvest of the cells is performed by the same principle as trypsination outside the bag.

Figure 3:
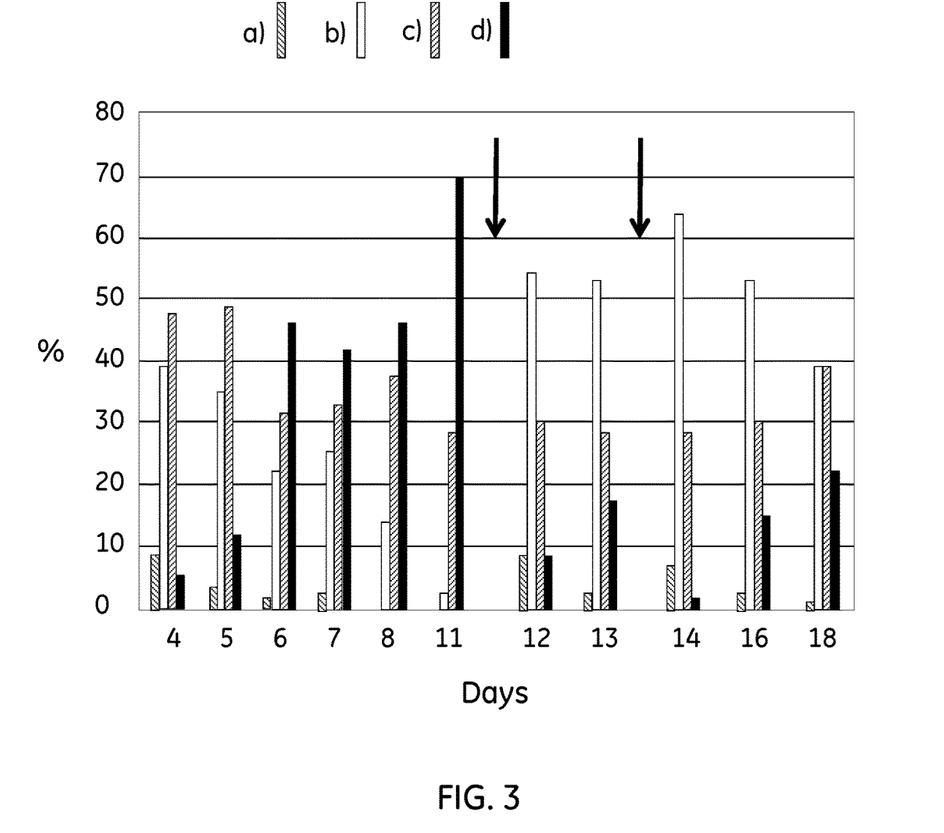
FIG. 3 shows the growth of bone marrow-derived human MSCs on CYTODEX™ 3 microcarriers in a WAVE™ plastic bag bioreactor after 4-18 days. Cells migrate between carriers and to empty carriers. Fresh empty carriers were added at 11 days and at 13 days. a) No cells on carriers, b) Solitary cells on carriers, c) Semi-confluent carriers, d) Confluent carriers.

Trypsination and addition of new carriers to increase surface area can be exchanged by adding new carriers directly to the culture and allowing the cells to migrate over to new carriers. Four days after addition of empty microcarriers to a MSC culture most carriers in the culture are populated with cells (FIGS. 2 and 3). The method of adding new carriers to a culture without a prior detachment step is particularly useful for MSCs, which are highly migratory in nature which was demonstrated as follows. GFP expressing MSCs and wild-type MSCs were seeded on CYTODEX™ 1 carriers in separate compartments, allowed to attached and then subsequently pooled after 24 hours. On day 4 the cells had migrated and GFP expressing and wild-type cells were found on 60% of the carriers. In a similar experiment GFP expressing MSCs and wild-type hMSCs were seeded on CYTODEX™ 3 carriers in separate compartments, allowed to attach and then subsequently pooled after 24 hours (FIG. 4). The ratio of carriers with only wild type hMSC decreased with time and was only 50% after 11 days of culture.

Example 2

Vero cells were obtained from ATCC (No. CCL81, ATCC-LGC Standards, Teddington, Middlesex TW11 0LY, UK). The cultivation medium was Dulbecco's modified eagle medium (DMEM)/Ham's F12 (GE Healthcare Life Sciences) supplemented with glucose (1 g/L), glutamine (0.9 g/L), β-cyclodextrin (0.1 g/L) (SIGMA™-Aldrich Co., St. Louis, Mo., USA) and soy peptone (2 g/L) (Kerry, Norwich, N.Y., USA). For bioreactor cultivations, pluronic F-68 was added (2 g/L) (Sigma-Aldrich Co.). For cell propagation, the cultivation medium was supplemented with FBS (50 g/L) (GE Healthcare Life Sciences). Inoculum was grown in T-flasks and NUNC™ CELL FACTORY™ systems (Thermo Fisher Scientific Inc., Waltham, Mass., USA). For detachment, cells were washed with PBS-EDTA and incubated with ACCUTASE™ (GE Healthcare Life Sciences).

In bioreactors, Vero cells were grown on CYTODEX™ 1 microcarriers (GE Healthcare Life Sciences) at a concentration of 3 g/L. The microcarriers were hydrated in PBS in a siliconized (SIGMACOTE™, Sigma-Aldrich Co.) glass vessel and then washed three times with PBS prior to autoclaving for 15 min at 121° C. Before transfer to WAVE™ Bioreactor, microcarriers were washed with cultivation medium. Cultures at 10 L scale were run in a WAVE™ Bioreactor 20/50 system (GE Healthcare Life Sciences). WAVEPOD™ II controller (GE Healthcare Life Sciences) was used to control temperature, pH, DO and agitation. The culture parameters were maintained at 37° C., pH 7.1, DO 30% and the agitation settings were 10 rpm/5°.

Cultures at 50 L scale were run in a WAVE™ Bioreactor 200 system (GE Healthcare Life Sciences). Cultivation conditions were the same as for the 10 L cultures except for the agitation setting, which were changed to 6 rpm/5°.

During bioreactor cultivation, samples were taken daily to determine cell concentration and morphology as well as concentrations of selected metabolites. Microcarrier suspension was withdrawn via the sample port while the base unit was rocking continuously. A 1 mL sample was transferred to a tube. After settling of the microcarriers, 800 µL, supernatant was removed and replaced with an equal volume of 0.1% crystal violet in 0.1 M citric acid and 1% TRITON™ X-100. The suspension was vigorously mixed for 45 sec and the released nuclei were counted using a hemocytometer. Cell morphology and attachment to microcarriers were determined using an inverted microscope with attached camera (Eclipse TS100, NIKON™ Instruments Inc., Melville, N.Y., USA). The concentration of glucose, lactate, glutamine, glutamate, and ammonium was measured in a Bioprofile FLEX™ (Nova Biomedical Corporation, Waltham, Mass., USA).

Inoculum grown in cell factories was used to seed a 10 L culture, which in turn was used to inoculate a 50 L culture by bead to bead transfer. The cells in the 10 L culture were detached with trypsin and transferred to new microcarriers in 50 L working volume. Prior to protease treatment, the cells were washed twice in PBS-EDTA.

The bead to bead transfer can be a manually and time consuming process. By using the separation device described above the trypsinisation can be performed in a closed system with less risk of contamination and a less labor intensive process.

Figure 8:
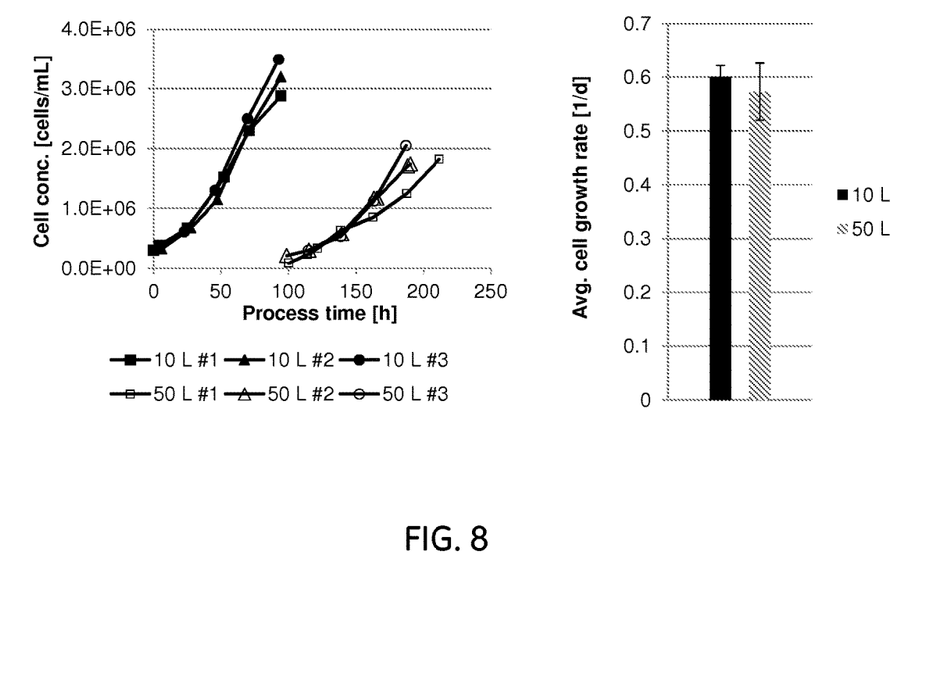
FIG. 8 shows the cultivation of Vero cells on CYTODEX™ 1 microcarriers.

The cell growth in 10 and 50 L cultures is shown in FIG. 8. Similar growth was observed in three consecutive processes. In the seed cultures, final cell concentrations of about 3E+06 cells/mL were achieved. Cells from the seed cultures were used to inoculate the 50 L production culture. A split ratio of 1:5 was used throughout this study. In both cultivation volumes, Vero cells attached to the microcarriers and started to grow without a lag phase. As shown in FIG. 8, the growth rates in the 10 and 50 L culture were similar. The 50

L cultures were grown to a cell concentration of about 2E+06 cells/mL for subsequent infection with influenza virus.

All publications, patent publications, and patents are herein incorporated by reference to the same extent as if each individual publication or patent was specifically and individually indicated to be incorporated by reference.

What is claimed is:

1. A method, comprising:
    a) adding mesenchymal stem cells in a cell culture medium and microcarriers to a bag bioreactor wherein the volume of added mesenchymal stem cells and microcarriers is between 150-300 ml, the seeding density is 1-10 adherent cells/microcarrier and the amount of microcarriers is at least 0.2 g (dry weight) per liter;
    b) allowing the mesenchymal stem cells to attach to the microcarriers while the bioreactor is kept in fixed position;
    c) adding additional cell culture medium to the bioreactor once the mesenchymal stem cells are attached;
    d) culturing the mesenchymal stem cells by agitation, to yield the cell culture; and
    e) increasing the surface area for continued culturing, wherein the step of increasing includes:
        i. securing the bag bioreactor in an angled upright position, at an opening in an upper corner of the bag bioreactor, by an external component such that the microcarriers are moved by gravity to a single corner inside the bag bioreactor opposite the upper corner;
        ii. collecting the microcarriers by sedimentation in the single corner of the bag bioreactor, the microcarriers having the mesenchymal stem cells attached thereon;
        iii. transferring the collected microcarriers to an external separation device using gravity flow or overpressure on the bag bioreactor
        iv. detaching the mesenchymal stem cells from the microcarriers inside the external separation device;
        v. separating the detached mesenchymal stem cells from the microcarriers by flowing, under agitation, a buffer through the external separation device;
        vi. adding new microcarriers and the detached mesenchymal stem cells to the bag bioreactor for continued culturing;
    f) harvesting the mesenchymal stem cells of step e) by active detachment and separation; wherein step e) is repeated until 3-8 g microcarriers per liter medium is reached; and wherein one therapeutic cell dose of mesenchymal stem cells can be produced per 2 liter of culture volume.

2. The method of claim 1, wherein the microcarriers are provided with magnetic particles.

3. The method of claim 1, wherein the mesenchymal stem cells are cells from adipose tissue, bone marrow or cord blood.

4. The method of claim 3, wherein the mesenchymal stem cells are adult mesenchymal stem cells.

5. The method of claim 1, wherein the mesenchymal stem cells are infected with a virus.

6. The method of claim 1, wherein the bag bioreactor is an inflated bioreactor bag.

7. The method of claim 1, wherein the mesenchymal stem cells are detached in step f, by using enzymes, thermo responsive agents, pH responsive agents, chelating agents and/or osmolality-changing agents.

8. The method of claim 7, wherein the mesenchymal stem cells detached in step f, by addition of a protease, such as trypsin.

9. The method of claim 1, wherein the external separation device comprises at least one screen with pores having circle-equivalent diameters larger than the average cell diameter and smaller than the average microcarrier diameter.

10. The method of claim 1, wherein the external separation device comprises a rotating agitator.

11. The method of claim 1, wherein the external separation device comprises a retentate compartment, separated from a permeate compartment by a screen sheet.

12. The method of claim 11, wherein the external separation device comprises a rotating agitator in the retentate compartment and the external separation device is positioned so that the retentate compartment is below the screen and the permeate compartment.

13. The method of claim 12, comprising a step of introducing the microcarriers in the retentate compartment under agitation, and adding a protease such as trypsin to the retentate compartment to allow the mesenchymal stem cells to detach from the microcarriers.

14. The method of claim 1, wherein the external separation device comprises one or more tubular screens.

15. The method of claim 14, wherein the external separation device comprises one or more tubular screens with the lumens fluidically connected to a retentate circuit and with a permeate compartment surrounding the one or more tubular screens.

16. The method of claim 14, wherein the external separation device comprises one or more tubular screens with the lumens fluidically connected to a permeate compartment and with a retentate compartment surrounding the one or more tubular screens.

* * * * *